United States Patent [19]

Hoffman

[11] Patent Number: 4,871,248
[45] Date of Patent: Oct. 3, 1989

[54] METHOD OF PARTICLE SIZE DETERMINATION

[75] Inventor: Richard L. Hoffman, Wilbraham, Mass.

[73] Assignee: Monsanto Company, St. Louis, Mo.

[21] Appl. No.: 84,271

[22] Filed: Aug. 11, 1987

[51] Int. Cl.⁴ ............................................. G01N 15/04
[52] U.S. Cl. ...................................... 356/36; 73/61.4; 356/427
[58] Field of Search ................. 356/36, 336, 426, 427; 73/61.4, 865.5

[56] References Cited

U.S. PATENT DOCUMENTS

| 3,475,968 | 11/1969 | Jones | 73/865.5 |
| 4,311,039 | 1/1982 | Koehler | 73/61.4 |
| 4,478,073 | 10/1984 | Holsworth et al. | 73/61.4 |

OTHER PUBLICATIONS

"Determination of the Particle Size Distribution of Powders by Means of Photosedimentograph" by J. M. Fortuin et al., 3/12/75.

"Particle Size Analysis by Sedimentation" by J. William Shelnutt 8/71.

"Horiba Particle Size Distribution Analyzer CA-PA-700".

Primary Examiner—Richard A. Rosenberger
Attorney, Agent, or Firm—R. Bruce Blance

[57] ABSTRACT

A process for particle size distribution analysis of a particulate substance of particle size in the range of 0.05 to 50 microns, which comprises a photosedimentation method using a horizontal rotating disc centrifuge and a narrow band of a dispersion of the particulate substance in juxtaposition to a column of clear sedimentation liquid.

8 Claims, 2 Drawing Sheets

METHOD OF PARTICLE SIZE DETERMINATION

This application is directed to a process for determining particle size distribution of a substance by photosedimentometry and more particularly it is directed to a process for determining particle size distribution by sedimentation using a horizontal rotating disc centrifuge.

Photosedimentation apparatus has been developed in the past for particle size distribution analysis of substances of particle size in the range of 0.01 to 100 microns. The Technidyne centrifugal photosedimentometer is an example of this instrument. It consists of a vertical drum rotating on a hollow spindle through which analytical samples can be introduced. The drum provides a chamber to contain the sedimentary fluid. Since the chamber is only partially filled with fluid, the liquid-vapor interface becomes a cylindrical surface coaxial with the axis of rotation. To start a run, particles are injected into the centrifuge, already spinning at a steady rate, in a manner which locates them at the liquid-vapor interface. Starting from this position the particles settle radially outward under conditions governed by Stokes' law. As a result, particles are separated by size with the largest settling at the fastest rate and the smallest settling at the slowest rate. At some radial position beyond the interface, the presence and amount of particles is continuously monitored as they settle by directing a narrow beam of light through the spinning drum and then into a photodetector and a treatment of the data based on Stoke's law and Beer's law is applied to determination of particle size and distribution.

The Technydyne photosedimentometer suffers from a number of disadvantages. It requires large quantities of sedimenting fluid which is often flammable or toxic and must be handled with caution. It does not allow determination of particle size for materials less dense than the sedimentary fluid. It requires from 1.5 to 4 hours to shut down the instrument, change the fluid and start up again.

Recently, particle size analyzers incorporating a horizontal rotating disc centrifuge have become commercially available from Horiba Ltd., Kyoto, Japan. A series of instruments, CAPA 300, CAPA 500 and CAPA 700 are all based on the principle of liquid phase photosedimentation applied to uniform dispersions of particles in the sedimenting fluid. The sample size is in the range of 2 to 4 ml, hence hazards from sedimenting fluids are minimized. The instrument is capable of fast shutdown and start-up. Hence little time is lost in aborted runs. The sample to be tested is entered into a small cuvette cell as a uniform dispersion of particles, and then the cell is placed in the centrifuge as shown in FIGS. 1 and 2 which illustrate in a plan drawing (FIG. 1), and cross-sectional view (FIG. 2), the centrifuge disc 1 with the sample cell 2 and a reference cell 3 inserted therein, and the collimated light beam 4 passes through the sample and then through an aperture 5 capable of admitting only unscattered light to photodetector 6. Next, the centrifuge is accelerated quickly up to a constant speed of rotation so that the particles in this instrument also settle under conditions governed by Stokes' law. In this case, however, the particles are settling from a uniform dispersion, so that one must monitor the depletion of particles with time as the larger particles settle more quickly than the small. This measurement is accomplished in a manner similar to the Technidyne photosedimentometer by directing a narrow light beam through the sample at a point intermediate to the ends of the cuvette cell.

At least two problems limit the accuracy of the data that one can obtain with the Horiba instruments. One that is serious, is the requirement for obtaining slopes of experimental data in the analysis. This leads to poor resolution of the data to give particle size. Another is the fact that the extinction coefficient is treated as a constant or has to be arbitrarily selected for a range of particle sizes. Setting the extinction coefficient to a constant is a gross over-simplification if there are particles less than one micron in size. Errors are also introduced if one arbitrarily selects a table of extinction coefficients without realizing that the refractive index ratio of the particles to the fluid also has an effect on the extinction coefficient.

These problems have now been overcome by the use of a line start in place of a uniform dispersion in the cuvette cell, and the application of Mie theory in the data analysis to account for the effect of particle size and the refractive index ratio between the particles and the fluid on the extinction coefficient. Thus there has been developed a method of particle size analysis of a substance comprising particles in the range of 0.05 to 50 microns, in a particle size distribution analyzer comprising (a) a horizontal rotating disc centrifuge in which sample cell and a reference cell are inserted and (b) an optical system for determination of light absorbance over an interval of time at a position intermediate to the top and bottom ends of the sample cell, wherein the method comprises dispersing the particulate substance in a liquid dispersion medium, filling the sample cell with a clear liquid which is miscible with the liquid dispersion medium and a narrow band of the dispersion situated at the top or bottom and of the cell, filling the reference cell with the clear liquid, inserting the sample and reference cells horizontally into the centrifuge so that the narrow band of the dispersion orients along a side of the sample cell, accelerating the centrifuge to a selected speed allowing the narrow band of the dispersion to reorientate at the top or bottom end of the sample cell and the particles of the dispersion to migrate therefrom to the opposite end of the sample cell under the influence of the centrifugal force, determining absorbance data of the sample cell during the time of migration of the particulate substance and determining the particle size distribution of the particulate substance from the absorbance data.

This method will appear more fully from the following detailed description, made in conjunction with the accompanying drawings.

FIGS. 3 and 4 illustrate the sample cell used with the disc centrifuge.

FIG. 5 illustrates the Teflon stopper which is used to seal the sample cell.

Figure 1:
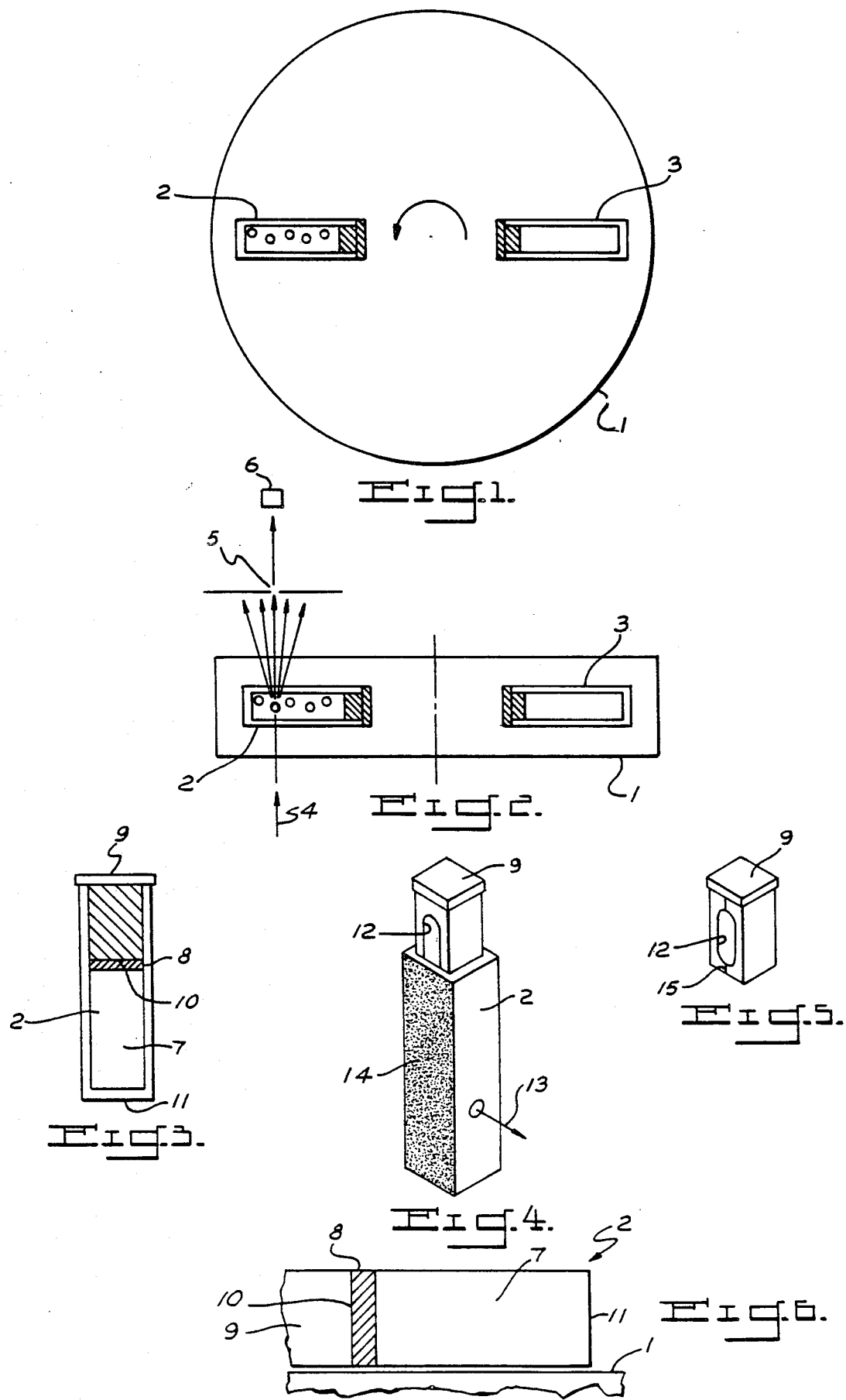
FIG. 1 is a simplified plan of the centrifuge disc.
Figure 2:
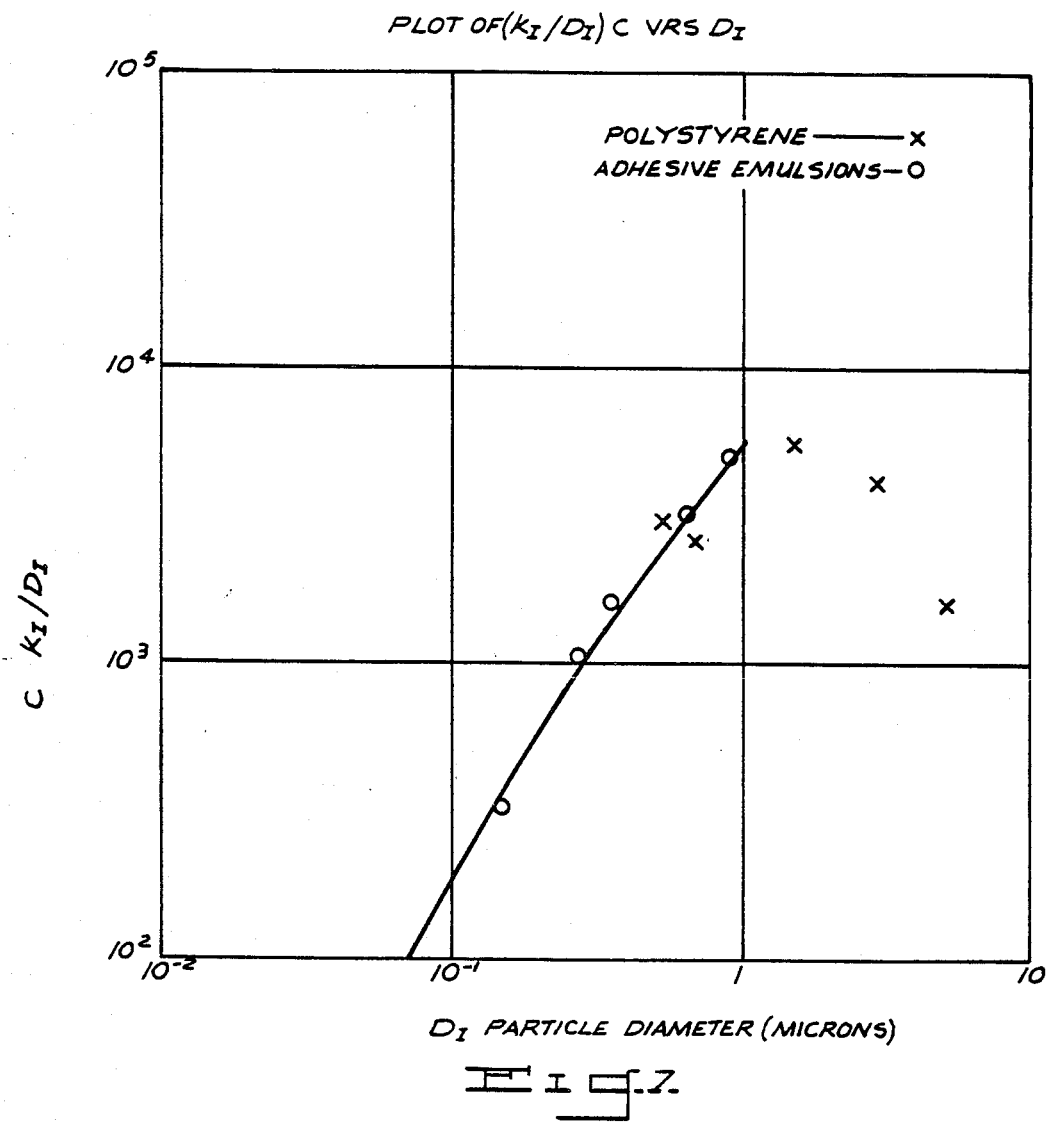
FIG. 2 is a simplified cross sectional view of the centrifuge disc.

FIG. 6 schematically illustrates the sample cell at the beginning of an analysis.

FIG. 7 shows a plot of particle diameter versus a correction factor for absorbance for a specific ratio of refractive index of particles to refractive index of sedimentation medium.

A line start is accomplished by placing a thin layer of the particles to be analyzed above or below a reservoir of the clear fluid into which they will migrate under the influence of the centrifugal force. To do this with the Horiba instruments, one must find a way which preserves the integrity of the thin layer when the cuvette containing the sample is turned from a vertical position to a horizontal position and is entered into the machine and then accelerated up to speed. The technique utilized involves the use of two different fluids, one for the layer (or band) of dispersed particles and the other for the clear fluid. The two fluids must be miscible and essentially non-solvents for the particles, and the liquid utilized in the top layer naturally has a density that is lower than the fluid below it. Choosing the viscosity and density differences carefully for the particles of interest, one can preserve the integrity of the thin band by this technique even though the band shifts to the side of the cuvette cell when it is placed horizontally in the centrifuge and then returns to the end of the cell as the centrifuge accelerates up to speed. Selection of fluids for polymer emulsions, and polystyrene particle standards illustrates the principles of selection.

For polymer emulsion particles and for particles such as the polystyrene standards which are obtained in water, a 50/50 mixture of methanol and water works well as a dispersing medium to form the thin band of dispersed particles over a clear column of water. For monomode distributions with narrow peaks, the initial weight fraction of particles in the dispersion medium can be as little as 0.00035 or possibly less to get adequate signal. Multimodal or broad distributions require higher concentrations for satisfactory instrument response.

Typical glass cuvette cells used with the Horiba instruments have a 1 cm × 1 cm internal cross-section and their length is 4.5 cm. One pair of opposite sides is clear while the other pair is frosted. A tight fitting Teflon stopper reduces the working length to 2 cm. A drawing of a cell in vertical position is given in FIG. 3 showing the cell 2 with the dispersion band 8 supernatant to the clear layer of sedimenting fluid 7 and stoppered with the Teflon stopper 9. The ends of the cell are identified as the top end 10 and the bottom end 11 in FIG. 3. In preparation for a run, a band of the dispersion is formed directly below the Teflon stopper; it sits on top of the column of the clear fluid through which the particles will settle.

Two techniques have been used to load the glass cuvette cell in preparation for a run. In one case the cell is loaded with the clear fluid and then the dispersion layer is placed on top of it. In the other case the dispersion layer is added first and then it is raised by adding the clear fluid beneath it. Disposable polyethylene pipettes may conveniently be used for either process. Which technique is ultimately used depends principally on the ease with which the interface can be formed. Interfaces which are difficult to form are most easily prepared using the latter technique.

The position of interface between the dispersion band and the clear fluid must be carefully located within the cuvette cell. This is facilitated by having a mark on the outside surface of the cell.

Using either of the two techniques previously mentioned to form the interface, one finds that some intermixing may occur between the two layers during this process. Such intermixing is easily corrected by placing the tip of a pipette at the interface and withdrawing fluid to sharpen the interface up. Vertical placement of the interface can be adjusted by adding or withdrawing clear fluid from the bottom layer. The thickness of the top layer can be adjusted in a similar manner.

Before the Teflon stopper is inserted in the cuvette cell, the thickness of the top layer should be set to the minimum that can be used without trapping air bubbles below the stopper. If too much of the dispersion from the top layer is displaced into the hole in the middle of the Teflon stopper (see FIG. 3), a false signal will occur in the particle size distribution. This false signal is generated by particles settling in the hole and then leaking past the sides of the stopper and into the settling chamber. Narrow channels cut in two sides of the Teflon stopper lead to the hole and enhance this leakage. But when the volume of fluid displaced into the hole in the stopper is kept small the effects of this leakage can be avoided by placing the channels so that they face the frosted sides of the cuvette cell in the manner illustrated in FIG. 4 which shows the sample cell 2 with the stopper 9 part way inserted into the cell so that the hole 12 faces the frosted side 14 of the cell. Under these circumstances particles which leak through the channels 15 shown in FIG. 5, go undetected by the light beam (FIG. 4, 13) and are insufficient in quantity to cause secondary flows in the cell.

Once the cell has been loaded, the run should be initiated without delay to minimize a baseline signal caused by particles which settle across the interface between the dispersion layer and the clear layer before the run is initiated. These particles get mixed with the clear fluid during startup. More accurately, the time that should be minimized is the time that elapses between sharpening the interface and starting up the run. Other factors which can be manipulated to minimize baseline signal are the viscosity and the density of the fluids used in the layers.

It is also important, however, not to rush the process of laying the cuvette cell on its side and inserting it in the centrifuge. Tipping the cell abruptly will cause undue mixing between the layers. This can be avoided if one takes roughly three to five seconds to slowly (and smoothly) tip the cell from a vertical to a horizontal position in the centrifuge chamber. More time is required if the fluids are more viscous. Fluids above about 100 cps can give spurious results.

In conjunction with the sample cell already discussed one must also have a reference cell in the centrifuge during all runs. Before the start of each run a blank measurement should be made using this cell and the sample cell following the procedures outlined in manuals provided by Horiba.

FIG. 6 illustrates schematically the sample cell 2, in horizontal position on the centrifuge disc 1, after the disc has reached a speed sufficient to cause the band of dispersed particles 8, to revert to the position between the clear sedimentary fluid 7 and the Teflon stopper 9 which it occupied when the cell was in a stationary, vertical position.

Since the centrifuge of the Horiba 500 instrument accelerates at a linear rate with time during the start-up phase of an analysis and since it has been calculated that at the final steady rotation of the centrifuge, particles require only one third the time to settle the distance settled during acceleration, time zero for an analytical run can be taken to be one third of the time required to accelerate from 0 to the selected steady state rate of rotation. Similar adjustments can be made for other instruments.

Practical ways of minimizing the initial baseline signal include a reduction of the density difference between the particles and the fluid of the dispersion layer, an increase in the viscosity of the fluid, and a reduction in the time between the point where the interface is sharpened and the run is initiated by turning on the centrifuge. Reducing the density difference has its limitations because inaccuracies in the values of numbers used for the density of the particles and the fluid are magnified when this is done. However, density differences as small as 0.025 g/ml can be successfully used.

Generally one can make runs which give baseline signals in the range of 20 to 80 millivolts when the sample signal ranges from over 300 to 800 millivolts. Under these conditions baseline editing is fairly easy to accomplish because the baseline signal is linear until the desired signal begins to come through. Thus one can place a straightedge along the baseline and determine the point at which it deviates from linearity. Signal up to this point is edited from the run. A recorder trace of the initial signal during a run is very useful for accomplishing the editing.

During an analysis the temperature of the samples has been found to rise to a constant value in an asymptotic fashion which varies with RPM. For example with the CAPA 500 at 5000 RPM this temperature rise amounts to about 8° C. It is less, of course, at lower RPM. When the temperature rise is enough to cause a significant change in the viscosity and density of the suspending fluid during a run, one must account for this change in some way that minimizes or eliminates the error that would otherwise be introduced into the particle size calculation. With settling fluids such as water and dimethyl formamide/acetone mixtures, one can make a satisfactory correction by using viscosity and density values which correspond to the average of the highest and the lowest temperatures that occur in the sample during the run. With water, for example, the error introduced into the particle size calculation by doing so is no greater than ±4.3%. This is the largest possible error incurred if the temperature rises 8° C. above an ambient temperature of 22° C.

Yet a better way to handle the problem seems to be through good ventilation in the centrifuge. With the centrifuge door left open, the temperature in the cuvette cell only rises to a maximum of 4.5° C. above the ambient temperature when the centrifuge spins at 5000 RPM. Using an average temperature value under these circumstances would reduce the errors to roughly half what they are when the door is closed. More sophisticated temperature control schemes could be devised, but the small gains that might be achieved do not seem to be worth the complication or effort.

Ideally the light beam used to detect particles in the cuvette cell as they settle should be infinitesimal in diameter and the depth of the band used to make the "line" start should also be infinitesimal. Under these conditions the instrument would be able to fully resolve any particle size distribution that might be tested. In reality, however, these two dimensions are finite. As a result the particle size distribution derived from the data may differ somewhat from the true distribution.

In the Horiba CAPA 500 the beam diameter appears to be between 2 and 3 mm; we have found it advantageous to use a 2 mm dispersion band to start the run. From experimental tests with various band depths, it is considered that the response obtained with a depth about one half to one times the beam diameter is satisfactory and about ⅔ is near the optimum. The peak height obtained with this depth is more than 80% of the maximum at any given particle concentration.

If the fluid in the dispersion band has a viscosity and density which differ from the clear sedimenting fluid in the cuvette cell, then the width of the band will, in effect, be altered. One can see this most easily by considering several extreme cases with a dispersion of monosized particles. If the settling rate for the particles is much much faster in the band than in the clear fluid, then it is evident that all the particles in the band will settle quickly to the interface between the two fluids before any of the particles can settle an appreciable distance in the clear fluid. In effect then, the run will have been initiated with a band of infinitesimal thickness. If on the other hand, the settling rate of the particles is much much faster in the clear fluid than in the band, then the run will appear to have been initiated with a band of almost infinite thickness. This is clearly an undesirable result.

Yet another case of interest is the one where particles settle with equal velocity in both the dispersion layer and in the clear fluid. Under these conditions the effective band width is, in fact, the band width used to initiate the run.

Keeping in mind the responses described above, one can see that it is best to select fluids for the dispersion band which give settling rates that are essentially equal to or greater than the settling rates in the clear fluid.

If one prepares a band of dispersed particles in the cuvette cell over a column of clear fluid in the usual manner and then allows the cell to stand on the bench top, streaming will be observed after a period of time. This phenomenon manifests itself as long fingers or streamers of dispersed particles which extend down below the dispersion band. At higher concentrations, round heads can generally be seen at the base of each streamer. The streamers settle at a much faster rate than the rate predicted by Stokes' law for individual particles.

Similar effects occur when particles settle under the influence of a centrifugal force field. Tests designed to explore this matter must be of a different sort than those described above since streamers cannot be viewed with ease when the cuvette cell is spinning in the centrifuge. One procedure that can be used, is to work with narrow monomodes and then look for a spread in the distribution curve as evidence of the streaming phenomenon. Streaming causes the apparent distribution to spread to larger sizes without changing the smallest size detected, and a spread in the distribution curve can be measured by the difference between the maximum and minimum sizes spanned by the curve. Two factors appear to have an effect on the streaming process. One is the concentration of the particles and the second is the rotational rate of the centrifuge. When the particle concentration of a monomode lies in the range of 0.0003 or less, streaming is apparently suppressed.

Particle concentrations below 0.0003 weight fraction as a way to suppress streaming, is an acceptable approach when the distribution is narrow, but it cannot be used with broader distributions because the absorbance signal will be too low. Higher particle concentrations must be used with broad distributions. Fortunately, however, it appears that another factor enters the picture to keep streaming from occurring. With broad distributions the particle concentration is reduced as the particles settle because the settling rate is a function of the particle size. Also streaming is reduced by increasing the rate of rotation of the centrifuge. Therefore even at much higher concentrations coupling the effect of a broad distribution with the effect of RPM, results free of streaming effects should be obtained.

Thus, when a sample with a broad distribution is being analyzed, a weight fraction of particles in the range of 0.003 or higher can be used without introducing substantial error due to streaming provided a centrifuge speed is selected above 2000 rpm and preferably above 3000 rpm. The presence of a broad distribution can be quickly ascertained by microscopic examination prior to commencing the particle size distribution analysis.

The particulate substance subjected to particle size analysis by the method herein may be organic or inorganic and requires only that it be insoluble in the dispersion liquid and the clear sedimentation liquid. The particles may be regular in shape or irregular when they are non-spherical, the method of analysis provides the effective Stokesian diameter of the particles.

The following examples illustrate the invention but are not intended to limit its scope.

EXAMPLE 1

A dispersion of an emulsion polymer in a 50/50 weight mixture of methanol and water was prepared at a weight fraction of polymer of 0.003. A 0.2 cm band of the dispersion was formed above a column of water in a cuvette of 1×1 cm cross-section by the bottom filling technique described hereinabove. The cuvette was carefully tilted to a horizontal position and inserted in the horizontal disc centrifuge of a Horiba CAPA 500 instrument, along with a reference cuvette containing water. The centrifuge was run at 5000 rpm and a trace of absorbance versus time was obtained. The data were converted to a plot of the relative amount of particles versus size based on the assumption that the extinction coefficient is a constant. The data were then corrected to account for the effect of particle size on the amount of light scattered by the particles by dividing $(K_i/D_i)C$ into the absorbance where $K_i$ is the Mie theory extinction coefficient averaged over the small spread of sizes in the measuring beam, $D_i$ is the average effective particle diameter in the light beam, and C is a constant. The need for this correction is evident from the Beer's law relationship:

$$\ln(I_0/I_i) \simeq \left[\frac{K_i}{D_i}\right]\left[\frac{3}{2} \times 10^4 \frac{L\rho_L}{\rho_P}\right] WFP_i.$$

where $I_0$ is the reference beam intensity without particles $I_i$ is the intensity of the beam passing through a sample containing particles of effective diameter $D_i$ at a concentration of $C_i$ L is the optical path length in cm.

$\rho_L$ is the density of the suspending fluid.

$\rho_P$ is the density of the particles.

$WFP_i$ is the weight fraction of particles of size i in the suspension. This equation applies when $WFP_i << 1$.

The relationship is derived by combining a Beer's law relationship for light scattering by particles with Mie theory extinction coefficients and a Stoke's Law relationship for sedimentation of particles. Values of $[K_i/D_i]$ C were obtained experimentally with monomode standards and were used to provide the graph of FIG. 7. Appropriate values of $[K_i/D_i]$ C were then taken from the graph and divided into the absorbance in Table 1 to provide the relative amounts of particles on a weight basis as a function of size.

TABLE 1

ANALYSIS OF EMULSION POLYMER

| D (microns) | Absorbance | $CK_i/D_i$ (5000 RPM) |
|---|---|---|
| 1.22 | .005 | 5700 |
| 1.18 | .024 | 5600 |
| 1.14 | .070 | 5490 |
| 1.10 | .134 | 5375 |
| 1.06 | .220 | 5200 |
| 1.02 | .322 | 5180 |
| .98 | .729 | 4900 |
| .94 | .717 | 7600 |
| .90 | .292 | 7500 |
| .86 | .146 | 7300 |
| .82 | .097 | 7100 |
| .78 | .073 | 3900 |
| .74 | .051 | 3700 |
| .70 | .047 | 3400 |
| .66 | .041 | 3250 |
| .62 | .041 | 3000 |
| .58 | .047 | 2840 |
| .54 | .053 | 2600 |
| .50 | .060 | 2400 |
| .46 | .083 | 2200 |
| .42 | .151 | 1900 |
| .38 | .512 | 1700 |
| .34 | .734 | 1450 |
| .30 | .492 | 1200 |
| .26 | .170 | 940 |
| .22 | .051 | 660 |
| .18 | .019 | 480 |
| .14 | 0.0 | 380 |

EXAMPLE 2

The process of Example 1 was applied to a polystyrene standard of particle size 2.95 micron using a 0.0003 weight fraction dispersion in a suspending fluid containing a 50/50 weight ratio of water and methanol. The sedimenting fluid was water. The disc centrifuge was run at 1000 rpm. Data are presented in Table 2. In successive runs the weight average diameter was determined to be 3.17 and 3.15 microns, the number average diameter was determined to be 2.90 and 2.90, the dispersity ratio of weight average to number average diameter was 1.096 and 1.086 and, the weight median diameter was 2.88 and 2.88.

TABLE 2

PARTICLE SIZE DISTRIBUTION OF A 2.95 MICRON POLYSTYRENE STANDARD IN THE HORIBA CAPA 500 VIA THE LINE START METHOD

| DIAMETER (MICRONS) | WT. FRAC. >DIA. | NO. FRAC. >DIA. | REL. WEIGHT PER UNIT DIA. |
|---|---|---|---|
| RUN 1 | | | |
| 7.783 | 0.000 | 0.000 | 0.000 |
| 7.411 | 0.001 | 0.000 | 0.002 |
| 7.054 | 0.002 | 0.000 | 0.003 |
| 6.716 | 0.003 | 0.000 | 0.003 |
| 6.389 | 0.007 | 0.001 | 0.007 |
| 6.084 | 0.012 | 0.001 | 0.010 |
| 5.792 | 0.018 | 0.002 | 0.013 |
| 5.511 | 0.025 | 0.003 | 0.014 |
| 5.245 | 0.034 | 0.004 | 0.019 |
| 4.992 | 0.044 | 0.006 | 0.022 |
| 4.751 | 0.055 | 0.009 | 0.025 |
| 4.522 | 0.068 | 0.012 | 0.033 |
| 4.304 | 0.084 | 0.017 | 0.039 |
| 4.096 | 0.103 | 0.024 | 0.052 |
| 3.899 | 0.126 | 0.034 | 0.071 |
| 3.711 | 0.156 | 0.048 | 0.090 |
| 3.532 | 0.193 | 0.068 | 0.131 |
| 3.362 | 0.250 | 0.105 | 0.195 |
| 3.200 | 0.308 | 0.148 | 0.164 |

TABLE 2-continued

PARTICLE SIZE DISTRIBUTION OF A 2.95 MICRON POLYSTYRENE STANDARD IN THE HORIBA CAPA 500 VIA THE LINE START METHOD

| DIAMETER (MICRONS) | WT. FRAC. >DIA. | NO. FRAC. >DIA. | REL. WEIGHT PER UNIT DIA. |
|---|---|---|---|
| 3.045 | 0.363 | 0.195 | 0.220 |
| 2.898 | 0.470 | 0.304 | 0.587 |
| 2.759 | 0.702 | 0.574 | 1.000 |
| 2.626 | 0.907 | 0.846 | 0.439 |
| 2.499 | 0.969 | 0.941 | 0.123 |
| 2.379 | 0.989 | 0.976 | 0.052 |
| 2.264 | 0.997 | 0.994 | 0.024 |
| 2.155 | 1.000 | 1.001 | 0.005 |
| 2.051 | 1.000 | 1.001 | −0.002 |
| 1.953 | 1.000 | 1.000 | −0.002 |

RUN 2

| 7.783 | 0.000 | 0.000 | 0.000 |
| 7.411 | 0.000 | 0.000 | 0.001 |
| 7.054 | 0.001 | 0.000 | 0.000 |
| 6.716 | 0.001 | 0.000 | 0.002 |
| 6.389 | 0.004 | 0.000 | 0.008 |
| 6.084 | 0.009 | 0.001 | 0.008 |
| 5.792 | 0.015 | 0.002 | 0.008 |
| 5.511 | 0.020 | 0.002 | 0.012 |
| 5.245 | 0.027 | 0.004 | 0.016 |
| 4.992 | 0.036 | 0.005 | 0.020 |
| 4.751 | 0.046 | 0.008 | 0.022 |
| 4.522 | 0.059 | 0.011 | 0.030 |
| 4.304 | 0.074 | 0.015 | 0.037 |
| 4.096 | 0.092 | 0.022 | 0.048 |
| 3.899 | 0.115 | 0.031 | 0.064 |
| 3.711 | 0.143 | 0.045 | 0.082 |
| 3.532 | 0.181 | 0.065 | 0.130 |
| 3.362 | 0.236 | 0.101 | 0.172 |
| 3.200 | 0.288 | 0.139 | 0.142 |
| 3.045 | 0.345 | 0.188 | 0.243 |
| 2.698 | 0.474 | 0.318 | 0.666 |
| 2.759 | 0.732 | 0.617 | 0.983 |
| 2.626 | 0.917 | 0.861 | 0.337 |
| 2.499 | 0.969 | 0.940 | 0.108 |
| 2.379 | 0.988 | 0.973 | 0.050 |
| 2.264 | 0.996 | 0.991 | 0.024 |
| 2.155 | 1.000 | 0.999 | 0.007 |
| 2.051 | 1.000 | 1.000 | −0.002 |

COMPARATIVE EXAMPLE 1

In contrast to example 2, determination of particle size of the polystyrene standard, was carried out by the uniform dispersion method conventionally used with the Horiba CAPA 500 instrument. A uniform dispersion of the polystyrene standard in water was used for the analysis. The data for three successive determinations are presented in Table 3. They show that results are generally erratic and irreproducible. Thus volume percent of particles of diameter in the range of 4.5 to 4.7 microns was 7.1, 1.6 and 0 respectively in the three runs; in the range of 3.5 to 3.7 microns, it was 6.4, 4.0 and 1.7 and in the range of 2.7 to 2.9 microns it was 2.8, 13.4 and 18.

TABLE 3

RESULTS FROM THREE CONSECUTIVE PARTICLE SIZE MEASUREMENTS ON A 2.95 μm POLYSTYRENE STANDARD IN THE HORIBA CAPA-500 VIA THE UNIFORM DISPERSION METHOD

| Distribution Table (By Vol.) | | | Distribution Table (By Vol.) | | | Distribution Table (By Vol.) | | |
|---|---|---|---|---|---|---|---|---|
| D (μm) | F (%) | R (%) | D (μm) | F (%) | R (%) | D (μm) | F (%) | R (%) |
| 5.30 | 19.4 | 19.4 | 5.30 | 26.4 | 26.4 | 5.30 | 13.4 | 13.4 |
| 5.30–5.10 | 3.7 | 23.1 | 5.30–5.10 | 3.3 | 26.7 | 5.30–5.10 | 1.6 | 15.0 |
| 5.10–4.90 | 1.5 | 24.6 | 5.10–4.90 | 0.0 | 29.7 | 5.10–4.90 | 4.4 | 9.4 |
| 4.90–4.70 | 0.0 | 24.6 | 4.90–4.70 | 7.1 | 36.9 | 4.90–4.70 | 4.6 | 24.0 |
| 4.70–4.50 | 7.1 | 31.7 | 4.70–4.50 | 1.6 | 38.5 | 4.70–4.50 | 0.0 | 24.0 |
| 4.50–4.30 | 7.7 | 39.4 | 4.50–4.30 | 1.0 | 39.5 | 4.50–4.30 | 4.4 | 28.3 |
| 4.30–4.10 | 9.2 | 48.6 | 4.30–4.10 | 4.4 | 43.9 | 4.30–4.10 | 0.0 | 28.3 |
| 4.10–3.90 | 3.0 | 51.7 | 4.10–3.90 | 0.3 | 44.2 | 4.10–3.90 | 1.1 | 29.4 |
| 3.90–3.70 | 1.2 | 52.8 | 3.90–3.70 | 5.3 | 49.6 | 3.90–3.70 | 2.2 | 31.6 |
| 3.70–3.50 | 6.4 | 59.3 | 3.70–3.50 | 4.0 | 53.5 | 3.70–3.50 | 1.7 | 33.3 |
| 3.50–3.30 | 2.7 | 62.0 | 3.50–3.30 | 0.9 | 54.4 | 3.50–3.30 | 4.7 | 37.9 |
| 3.30–3.10 | 5.0 | 67.0 | 3.30–3.10 | 3.0 | 57.4 | 3.30–3.10 | 6.6 | 44.6 |
| 3.10–2.90 | 2.0 | 69.2 | 3.10–2.90 | 5.7 | 63.1 | 3.10–2.90 | 12.3 | 56.8 |
| 2.90–2.70 | 2.8 | 72.0 | 2.98–2.70 | 13.4 | 76.5 | 2.98–2.70 | 18.0 | 74.8 |
| 2.70–2.50 | 7.2 | 79.2 | 2.70–2.50 | 7.2 | 83.7 | 2.70–2.50 | 14.9 | 89.7 |
| 2.50–2.30 | 9.3 | 88.5 | 2.50–2.30 | 4.0 | 87.7 | 2.50–2.30 | 5.3 | 95.1 |
| 2.30–2.10 | 5.6 | 94.2 | 2.30–2.10 | 4.8 | 92.4 | 2.30–2.10 | 1.2 | 96.2 |
| 2.10–1.90 | 4.1 | 98.3 | 2.10–1.90 | 0.6 | 93.1 | 2.10–1.90 | 0.4 | 96.7 |
| 1.90–1.70 | 0.9 | 99.2 | 1.90–1.70 | 3.6 | 96.7 | 1.90–1.70 | 2.4 | 99.1 |
| 1.70–1.50 | 0.2 | 99.4 | 1.70–1.50 | 1.8 | 98.5 | 1.70–1.50 | 0.3 | 99.4 |
| 1.50–1.30 | 0.3 | 99.7 | 1.50–1.30 | 1.2 | 99.7 | 1.50–1.30 | 0.2 | 99.5 |
| 1.30–0.00 | 0.3 | 100.0 | 1.30–0.00 | 0.3 | 100.0 | 1.30–0.00 | 0.5 | 100.0 |
| D(AVE) | 4.01 | (PM) | D(AVE) | 3.68 | (PM) | D(AVE) | 3.01 | (PM) |

I claim:

1. A method of particle size analysis of a substance comprising particles in the range of 0.05 to 50 microns, in a particle size distribution analyzer comprising (a) a horizontal rotating disc centrifuge in which a sample cell and a reference cell are inserted and (b) an optical system for determination of light absorbance over an interval of time at a position intermediate to the top and bottom ends of the sample cell, wherein the method comprises dispersing the particulate substance in a liquid dispersion medium, filling the sample cell with a clear liquid which is miscible with the liquid dispersion medium and a narrow band of the dispersion situated at the top or bottom of the cell, filling the reference cell with the clear liquid, inserting the sample and reference cells horizontally into the centrifuge so that the narrow band of the dispersion orients along a side of the sample cell, accelerating the centrifuge to a selected speed allowing the narrow band of the dispersion to reorientate at the top or bottom end of the sample cell and the particles of the dispersion to migrate therefrom to the opposite end of the sample cell under the influence of the centrifugal force, determining absorbance data of the sample cell during the time of migration of the particulate substance and determining the particle size distribution of the particulate substance from the absorbance data.

2. The method of claim 1 wherein the density difference between the particulate substance and the clear liquid is at least 0.025 g/ml.

3. The method of claim 1 wherein the concentration of particulate substance in the dispersion liquid is initially in the range of 0.035 to 0.3% by weight.

4. The method of claim 1 wherein the dispersion is less dense than the clear liquid and is carefully added to a column of the clear liquid in the sample cell to provide a supernatant layer and wherein the integrity of the supernatant layer is maintained by stoppering the cell and slowly tilting it to a horizontal position in the disc centrifuge.

5. The method of claim 1 wherein the dispersion is less dense than the clear liquid, wherein a narrow band of dispersion is formed by first adding it to the sample cell and then adding a column of the clear liquid and wherein the integrity of the supernatant layer is maintained by stoppering the cell and slowly tilting it to a horizontal position in the disc centrifuge.

6. The method of claim 1 wherein the depth of the narrow band of dispersion is in the range of about one half to one times the beam diameter of the optical system.

7. The method of claim 1 wherein the clear liquid is a polymer solution.

8. The method of claim 1 wherein the particulate substance is a polymer.

* * * * *